United States Patent
Wang et al.

(10) Patent No.: US 10,308,930 B2
(45) Date of Patent: Jun. 4, 2019

(54) METHODS TO ACCELERATE ANTIBODY DIVERSIFICATION

(71) Applicant: ALBERT EINSTEIN COLLEGE OF MEDICINE, INC., Bronx, NY (US)

(72) Inventors: Xiaohua Wang, Bronx, NY (US); Matthew Scharff, Larchmont, NY (US)

(73) Assignee: Albert Einstein College of Medicine, Bronx, NY (US)

(*) Notice: Subject to any disclaimer, the term of this patent is extended or adjusted under 35 U.S.C. 154(b) by 0 days.

(21) Appl. No.: 15/514,052

(22) PCT Filed: Nov. 5, 2015

(86) PCT No.: PCT/US2015/059130
§ 371 (c)(1),
(2) Date: Mar. 24, 2017

(87) PCT Pub. No.: WO2016/073660
PCT Pub. Date: May 12, 2016

(65) Prior Publication Data
US 2018/0179516 A1     Jun. 28, 2018

Related U.S. Application Data

(60) Provisional application No. 62/076,099, filed on Nov. 6, 2014.

(51) Int. Cl.
| | |
|---|---|
| *A61K 48/00* | (2006.01) |
| *C07H 21/02* | (2006.01) |
| *C07H 21/04* | (2006.01) |
| *C12N 15/10* | (2006.01) |
| *C07K 16/00* | (2006.01) |
| *C07K 14/005* | (2006.01) |
| *C12N 9/78* | (2006.01) |
| *C12N 15/113* | (2010.01) |
| *C12N 15/86* | (2006.01) |

(52) U.S. Cl.
CPC ........ *C12N 15/1024* (2013.01); *C07K 14/005* (2013.01); *C07K 16/00* (2013.01); *C12N 9/78* (2013.01); *C12N 15/113* (2013.01); *C12N 15/86* (2013.01); *C07K 2317/14* (2013.01); *C07K 2319/80* (2013.01); *C12N 2310/14* (2013.01); *C12N 2310/531* (2013.01); *C12N 2710/10043* (2013.01); *C12N 2740/15043* (2013.01)

(58) Field of Classification Search
CPC ........................... A61K 31/713; C12N 15/111
See application file for complete search history.

(56) References Cited

U.S. PATENT DOCUMENTS

2006/0019241 A1* 1/2006 Ganapathy et al. .. C12N 15/111
2013/0059931 A1   3/2013 Petersen-Mahrt et al.
2013/0336934 A1* 12/2013 Crawford et al. ... A61K 31/713

OTHER PUBLICATIONS

PCT International Search Report and Written Opinion, dated Feb. 5, 2016 in connection with PCT International Application No. PCT/US2015/59130, 11 pages.
Kundu R et al., entitled "Expression of the Human Immunodeficiency Virus-Tat Gene in Lymphiod Tissues of Transgenic Mice is Associated with B-Cell Lymphoma," Blood, vol. 94, No. 1, Jul. 1, 1999, pp. 275-282.
Mouquet H et al., entitled "Memory B Cell Antibodies to HIV-1 gp140 Cloned from Individuals Infected with Clade A and B Viruses," PLoS One, Sep. 8, 2011, vol. 6, Issue 9, e24078, pp. 1-14.
Wang H et al., entitled "A source of the single-stranded DNA substrate for activation-induced deaminase during somatic hypermutation," Nature Communications, Jun. 13, 2014, vol. 5, Issue 4137, pp. 1-11.

* cited by examiner

*Primary Examiner* — Amy H Bowman
(74) *Attorney, Agent, or Firm* — Amster, Rothstein & Ebenstein LLP

(57) ABSTRACT

Methods for increasing somatic hypermutation of antibodies, especially in vitro expression of an isolated retroviral protein in an isolated mammalian immunoglobulin-producing cell, are provided.

18 Claims, 5 Drawing Sheets

METHODS TO ACCELERATE ANTIBODY DIVERSIFICATION

CROSS REFERENCE TO RELATED APPLICATION

This application is a U.S. national stage entry under 35 U.S.C. § 371 of PCT International Patent Application No. PCT/US2015/059130, filed Nov. 5, 2015, which claims benefit of U.S. Provisional Application No. 62/076,099, filed Nov. 6, 2014, the contents of each of which are incorporated herein by reference into the subject application.

BACKGROUND OF THE INVENTION

Throughout this application various publications are referred to in square brackets. Full citations for these references may be found at the end of the specification. The disclosures of these publications, and all patents, patent application publications and books referred to herein, are hereby incorporated by reference in their entirety into the subject application to more fully describe the art to which the subject invention pertains.

Antibodies are superior therapeutic reagents because of their wide range of biological functions, naturally evolved sustainable half-life and comparatively good safety. The effectiveness and success of an antibody-mediated therapy rely heavily on the specificity and affinity of the antibody against cognate antigens. Thus, obtaining antibodies with clinical application potential for designated therapeutic target represents a major hurdle in current bio-pharmacological industry.

Platforms to diversify antibodies in vitro offer a valuable alternative to traditional immunization based antibody production approach. They offer the possibility to overcome the hurdle encountered by the host immune system during the immunization process such as low immunogenicity, fast antigen degradation, immune dominancy etc. Currently, phage display and *E. coli* based gene expression library are the two main in vitro methods for antibody diversification. However, these processes do not provide post-translational modifications that are important for antibody binding and do not take advantage of antibody scaffolds that are evolutionarily evolved to provide high specific antibody-antigen interactions.

Vertebrate cells that undergo constitutive somatic hypermutation (SHM) at antibody gene loci have been shown to have the potential of generating de novo antibody against the model antigen streptavidin. However, the mutation frequency of those cells is 1-2 log scale lower than the somatic hypermutation (SHM) process that occurs in normal germinal center B cells in vivo. Therefore, commercial application of eukaryotic cell based antibody diversification process using physiological affinity maturation mechanism such as AID mediated mutation and error-prone DNA damage repair to generate a de novo antibody from an immunoglobulin gene that does not encode an antibody and that recognizes a predetermined antigen has been difficult, and still requires an the increase of in vitro SHM rate.

Over expression of the B cell endogenous genomic mutating factor activation induced deaminase (AID) in human Ramos cell lines can increase SHM rate at immunoglobulin gene (Ig) loci (FIG. 1) less than 10 fold. However, due to the genotoxicity of AID, further improvement of mutation rate just based on the modulation of the level or the activity of AID and its related molecules has been difficult to achieve. Some microbial products, such as LPS, have been suggested to increase AID level in B cells but there has been no evidence that these reagents can increase SHM rate in B cells in vitro. Thus, alternative approaches to enhance SHM at Ig loci are urgently needed to help establish eukaryotic cell-based antibody diversification platforms that offer a clear advantage over techniques currently available in the market.

The present invention addresses the need for alternative approaches to enhance the antibody diversification process through SHM at Ig loci, especially in vitro.

SUMMARY OF THE INVENTION

A method is provided of increasing somatic hypermutation of an immunoglobulin loci comprising effecting expression of an isolated retroviral protein in (i) an isolated mammalian immunoglobulin-producing cell, or (ii) an isolated immunoglobulin-producing cell of a cell line derived from a mammal, in an amount effective to increase somatic hypermutation of an immunoglobulin loci.

Also provided is a method of increasing somatic hypermutation of an immunoglobulin loci comprising (1) effecting expression of an isolated retroviral protein in (i) an isolated mammalian immunoglobulin-producing cell, or (ii) an isolated immunoglobulin-producing cell of a cell line derived from a mammal, and (2) reducing expression of Spt5 in the cell of (1), in an amount effective to increase somatic hypermutation of an immunoglobulin loci.

Also provided is a eukaryotic cell transformed to express an HIV Tat and over-express an activation induced deaminase (AID) and/or and comprising a knockdown of Spt5, wherein the cell comprises a heterogeneous nucleic acid encoding an immunoglobulin.

Also provided is a kit for increasing the rate of somatic hypermutation of an immunoglobulin loci in a eukaryotic cell comprising of an immunoglobulin loci, wherein the kit comprises a vector encoding an HIV Tat, reagents for use in transfecting a eukaryotic cell therewith, and written instructions for use.

This invention provides a method to use protein products from viruses to increase the efficacy of the diversification process of immunoglobulin gene by SHM in eukaryotic cells through their interaction with the eukaryotic transcription machinery.

This invention provides a method to increase the efficacy of the diversification process of immunoglobulin genes through SHM in eukaryotic cells by the combinatorial application of microbial products and the interference of cellular factors that are not generated from the microbes.

This invention provides a method to use microbial products in combination with the manipulation of cellular factor to enhance SHM in eukaryotic cells (such as the human Ramos B cell line) to meet the needs of generating eukaryotic cell-based antibody diversification platforms for de novo antibody generation against designated proteins or epitopes.

DETAILED DESCRIPTION OF THE INVENTION

Figure 1:
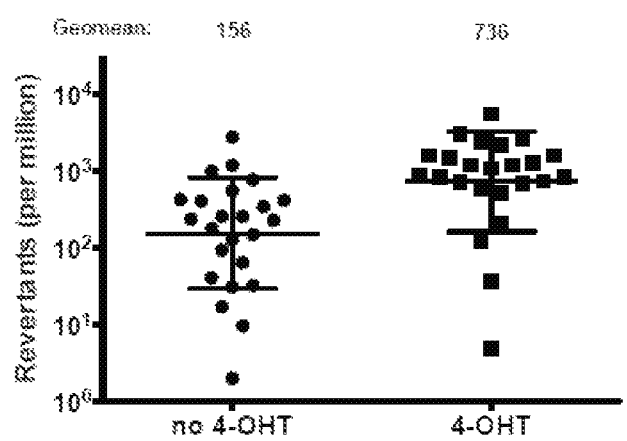
FIG. 1: Limited enhancement of SHM rate upon the increase of the abundance of nuclear AID: A subclone of the Ramos cell line bearing an early stop codon for translation and hence is negative for surface IgM staining was transduced with AID-ER gene. Without 4-hydroxyl-tamoxifen, endogenous AID molecule will generate IgM+ daughter cells through its introduction of mutation of the early stop codon. When 4-hydroxyl-tamoxifen is added in the system, the nuclear AID level will increase due to the nuclear translocation of exogenous AID-ER fusion protein in addition to those endogenous AID molecules. The figure shows that exogenous AID-ER fusion protein enhances the generation of IgM+ daughter cell frequency (revertants) ~4 fold upon its translocation into nucleus.

Herein is described invention that provides a method to use microbial products to increase the efficacy of the diversification process of the immunoglobulin gene through SHM in eukaryotic cells.

This invention provides a further method to increase the efficacy of the diversification process of immunoglobulin genes through SHM in eukaryotic cells by the combinatorial application of microbial products and the enhancing effect on SHM through the interference of cellular factors that are not generated from the microbes.

A method is provided of increasing somatic hypermutation of an immunoglobulin loci comprising effecting expression of an isolated retroviral protein in (i) an isolated mammalian immunoglobulin-producing cell, or (ii) an isolated immunoglobulin-producing cell of a cell line derived from a mammal, in an amount effective to increase somatic hypermutation of an immunoglobulin loci.

In an embodiment, the method is performed in vitro.

In an embodiment, as used herein, increasing somatic hypermutation means increasing relative to the level of somatic hypermutation of the immunoglobulin loci in the absence of the expressed isolated retroviral protein in the cell.

In an embodiment, expression is effected in an isolated mammalian immunoglobulin-producing B cell. In an embodiment, expression is effected in the isolated immunoglobulin-producing cell of a cell line derived from a mammal. In an embodiment, the isolated immunoglobulin-producing cell of a cell line derived from a mammal is a cell that does not constitutively express immunoglobulins, but which has been genetically engineered to express immunoglobulins.

In an embodiment of the methods, the cell has been genetically engineered to express more than one immunoglobulin type. In an embodiment, the cell has been genetically engineered to express only one immunoglobulin type.

In an embodiment, the isolated immunoglobulin-producing cell of a cell line derived from a mammal is a Ramos cell line. In an embodiment, the isolated immunoglobulin-producing cell of a cell line derived from a mammal is a hybridoma.

In an embodiment, the cell secretes immunoglobulins.

In an embodiment, the cell expresses immunoglobulins on a cell surface thereof.

In an embodiment, the expression of the isolated retroviral protein in the cell is effected by contacting the cell with a vector encoding the isolated retroviral protein. In an embodiment of the contacting, expression is effected by transfecting the cell with a vector encoding the isolated retroviral protein. In an embodiment, the contacting of the cell with a vector encoding the isolated retroviral protein is brought about artificially by the hand of man.

In an embodiment, the isolated retroviral protein is an HIV Tat protein.

In an embodiment, the vector is a lentiviral vector.

In an embodiment, the vector is an adenoviral vector.

In an embodiment, the expression of an exogenous HIV Tat protein in the cell is effected by contacting the cell with a pCDNA-tat eukaryotic expression vector encoding the exogenous HIV Tat protein.

In an embodiment, the method further comprises recovering one or more immunoglobulins produced by the cell of (i) or (ii) subsequent to effecting expression of the isolated retroviral protein therein.

In an embodiment, the method further comprises comprising screening the one or more immunoglobulins for activity against a predetermined antigen. The predetermined antigen may be a peptide, polypeptide, protein, carbohydrate, or other antigenic molecule.

Also provided is a method of increasing somatic hypermutation of an immunoglobulin loci comprising (1) effecting expression of an isolated retroviral protein in (i) an isolated mammalian immunoglobulin-producing cell, or (ii) an isolated immunoglobulin-producing cell of a cell line derived from a mammal, and (2) reducing expression of Spt5 in the cell of (1), in an amount effective to increase somatic hypermutation of an immunoglobulin loci.

In an embodiment, reducing expression of Spt5 in the cell of (i) is effected by contacting the cell with a RNAi nucleic acid directed to Spt5.

In an embodiment, the RNAi nucleic acid directed to Spt5 is a siRNA or an shRNA.

In an embodiment, the RNAi nucleic acid is an shRNA delivered by a vector.

In an embodiment, expression is effected in an isolated mammalian immunoglobulin-producing B cell.

In an embodiment, expression is effected in the isolated immunoglobulin-producing cell of a cell line derived from a mammal.

In an embodiment, the isolated immunoglobulin-producing cell of a cell line derived from a mammal is a cell that does not constitutively express immunoglobulins, but which has been genetically engineered to express immunoglobulins.

In an embodiment, the isolated immunoglobulin-producing cell of a cell line derived from a mammal is a Ramos cell line.

In an embodiment, the isolated immunoglobulin-producing cell of a cell line derived from a mammal is a hybridoma.

In an embodiment, the cell secretes immunoglobulins.

In an embodiment, the cell expresses immunoglobulins on a cell surface thereof.

In an embodiment, the expression of the isolated retroviral protein in the cell is effected by contacting the cell with a vector encoding the isolated retroviral protein.

In an embodiment, the isolated retroviral protein is an HIV Tat protein.

In an embodiment, the vector is a lentiviral vector.

In an embodiment, the vector is an adenoviral vector.

In an embodiment, the expression of an exogenous HIV Tat protein in the cell is effected by contacting the cell with a pCDNA-tat eukaryotic expression vector encoding the exogenous HIV Tat protein.

In an embodiment, the method further comprises recovering one or more immunoglobulins produced by the cell of (i) or (ii) subsequent to effecting expression of the isolated retroviral protein therein.

In an embodiment, the method further comprises screening the one or more immunoglobulins for activity against a predetermined antigen.

In an embodiment, the methods further comprises obtaining the hybridoma by fusing an immortal cell with a spleen cell of a non-human mammal that has been exposed to a predetermined antigen, and wherein the hybridoma has been determined to produce an immunoglobulin that binds the predetermined antigen.

In an embodiment, the method is performed in vitro.

In an embodiment, the cell has been treated to effect over-expression of activation induced deaminase (AID) as compared to expression of AID in a cell not so treated.

In an embodiment, the immunoglobulin loci of the somatic hypermutation increase comprises an IgH-V region.

Also provided is a eukaryotic cell transformed to express an HIV Tat and over-express an activation induced deaminase (AID) and/or and comprising a knockdown of Spt5, wherein the cell comprises a heterogeneous nucleic acid encoding an immunoglobulin.

Also provided is a kit for increasing the rate of somatic hypermutation of an immunoglobulin loci in a eukaryotic cell comprising of an immunoglobulin loci, wherein the kit comprises a vector encoding an HIV Tat, reagents for use in transfecting a eukaryotic cell therewith, and written instructions for use.

In an embodiment, the cell has been manipulated to increase the expression level or enzymatic activity of the B cell specific mutator-activation induced deaminase (AID) (U.S. Pat. No. 5,885,827 and Patent Application Publication No. US20060019262 A1, the contents of each of which are hereby incorporated by reference). The effect of this on SHM is limited to ~5 fold increase which is still significantly lower than the desired SHM rate that is achieved by germinal center B cells.

In an embodiment, the microbial products can be Tat protein of the Human Immunodeficiency Virus (HIV)-1 comprising the following sequence:

```
                                            (SEQ ID NO: 1)
MEPVDPRLEP WKHPGSQPKT PCTKCYCKKC CLHCQVCFMT
KGLGISYGRK KRRQRRRAPQ DNKNHQVSLS KQPTSRARGD
PTGQEESKEK VEKETVVDPV T.
```

In an embodiment, the HIV-1 Tat comprises the sequence set forth in NCBI Reference Sequence: GenBank: AAF35362.1.

In an embodiment, the HIV Tat protein comprises the following sequence:

```
                                            (SEQ ID NO: 2)
MEPVDPRLEP WKHPGSQPKT ACTNCYCKKC CFHCQVCFIT
KALGISYGRK KRRQRRRAHQ NSQTHQASLS KQPTSQPRGD PTGPKE.
```

In an embodiment, the HIV Tat comprises the sequence set forth in NCBI Reference Sequence: NP_057853.1. HIV Tat sequences are well known in the art and easily identifiable.

In an embodiment, the microbial products can also be other coding sequences diverged from HIV-1 Tat sequence such as a truncated version (86aa format or 72aa format of Tat) and any other mutated form of the sequences that maintains the functional interaction to eukaryotic transcriptional machinery.

In an embodiment, the microbial products can also be other retro-viral proteins such as the Tat protein from another subfamily of HIV like HIV-2 or other viruses that can functionally interact with eukaryotic transcriptional machinery.

In an embodiment, the microbial products can further be expanded to any bio-product generated by microbial species such as proteins, glycol-proteins, lipids, glycans, peptidoglycans, polysaccharides, nucleotides and chemicals that interfere with the transcription process in the cells.

In an embodiment, the eukaryotic cell can be: (i) B cell lines that undergo SHM constitutively and spontaneously, for example the human Ramos cell line; or ii) any cell line in (i) that has been manipulated to increase the expression level or enzymatic activity of the B cell specific mutator-activation induced deaminase (AID) (U.S. Pat. No. 5,885,827 and Patent Application Publication No. US20060019262 A1, the contents of each of which are hereby incorporated by reference); or (iii) any cell line that is not derived from constitutively mutating B cells and is genetically engineered to express an immunoglobulin gene and undergo a mutagenesis process upon the expression of AID or other APOPEC family members, or, alternatively, their derivatives; or iv) ex vivo B cells isolated from animal (preferably mammalian) or human tissue.

In an embodiment, the eukaryotic cell can also be: i) a eukaryotic B cell line bearing immunoglobulin gene in the endogenous genomic loci (such as the human Ramos B cells used in the example hereinbelow); or ii) an otherwise non-antibody producing cell which has been transfected to express an immunoglobulin (in non limiting examples, 293T cells or CHO cells that are used to produce commercial therapeutic antibodies).

In an embodiment, the delivery of the microbial products to the eukaryotic cell can be achieved by i) physical transfection of the cell using DNA or RNA fragments of the gene that encodes designated product by, in non-limiting examples, electroporation or liposome mediated transfection; or ii) viral mediated transduction of the cell using DNA or RNA fragments of the gene that encodes designated product using, in non-limiting examples, a lentivirus, retrovirus or adenovirus; or iii) direct application of purified microbial product to the cells such as recombinant Tat or Tat mediated transmembrane delivery; or iv) direct injection of a microbial product into the eukaryotic cells; or v) stable integration of the gene that encodes designated product into pluripotent stem cells or hematopoietic stem cells to generate B cells through further differentiation.

In an embodiment, the eukaryotic cell is otherwise a non-antibody producing cell, but has been transformed to express an immunoglobulin. In an embodiment, the immunoglobulin produced has the Fc sequence of a human Fc sequence.

In an embodiment, the Spt5 is a mammalian Spt5. In an embodiment, the Spt5 is a human Spt5. In an embodiment, the Spt5 has the following sequence, or is a recognized Spt5 variant thereof, for example, as listed in PubMed databases:

```
                                           (SEQ ID NO: 3)
MSDSEDSNFS  EEEDSERSSD  GEEAEVDEER  RSAAGSEKEE

EPEDEEEEEE  EEEYDEEEEE  EDDDRPPKKP  RHGGFILDEA

DVDDEYEDED  QWEDGAEDIL  EKASNIDNVV  LDEDRSGARR

LQNLWRDQRE  EELGEYYMKK  YAKSSVGETV  YGGSDELSDD

ITQQQLLPGV  KDPNLWTVKC  KIGEERATAI  SLMRKFIAYQ

FTDTPLQIKS  VVAPEHVKGY  IYVEAYKQTH  VKQAIEGVGN

LRLGYWNQQM  VPIKEMTDVL  KVVKEVANLK  PKSWVRLKRG

IYKDDIAQVD  YVEPSQNTIS  LKMIPRIDYD  RIKARMSLKD

WFAKRKKFKR  PPQRLFDAEK  IRSLGGDVAS  DGDFLIFEGN

RYSRKGFLFK  SFAMSAVITE  GVKPTLSELE  KFEDQPEGID

LEVVTESTGK  EREHNFQPGD  NVEVCEGELI  NLQGKILSVD

GNKITIMPKH  EDLKDMLEFP  AQELRKYFKM  GDHVKVIAGR

FEGDTGLIVR  VEENFVILFS  DLTMHELKVL  PRDLQLCSET

ASGVDVGGQH  EWGELVQLDP  QTVGVIVRLE  RETFQVLNMY

GKVVTVRHQA  VTRKKDNRFA  VALDSEQNNI  HVKDIVKVID

GPHSGREGEI  RHLFRSFAFL  HCKKLVENGG  MFVCKTRHLV

LAGGSKPRDV  TNFTVGGFAP  MSPRISSPMH  PSAGGQRGGF

GSPGGGSGGM  SRGRGRRDNE  LIGQTVRISQ  GPYKGYIGVV

KDATESTARV  ELHSTCQTIS  VDRQRLTTVG  SRRPGGMTST

YGRTPMYGSQ  TPMYGSGSRT  PMYGSQTPLQ  DGSRTPHYGS

QTPLHDGSRT  PAQSGAWDPN  NPNTPSRAEE  EYEYAFDDEP

TPSPQAYGGT  PNPQTPGYPD  PSSPQVNPQY  NPQTPGTPAM

YNTDQFSPYA  APSPQGSYQP  SPSPQSYHQV  APSPAGYQNT

HSPASYHPTP  SPMAYQASPS  PSPVGYSPMT  PGAPSPGGYN

PHTPGSGIEQ  NSSDWVTTDI  QVKVRDTYLD  TQVVGQTGVI

RSVTGGMCSV  YLKDSEKVVS  ISSEHLEPIT  PTKNNKVKVI

LGEDREATGV  LLSIDGEDGI  VRMDLDEQLK  ILNLRFLGKL  LEA.
```

Knockdown of Spt5, for example by knockout technology or by RNAi techniques such as siRNA or shRNA is a straightforward technical effect to obtain by one of ordinary skill in the art.

In an embodiment, the interference of cellular factors that enhances SHM can also be other factors that influence SHM level such as DNA isotopomerase I (TOPO I), Chk1, PTBP-2 or over expression of other factors.

In an embodiment, the cell line is an isolated human cell line. In an embodiment, the cell line or the cell is not present in a human subject.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

The following experiments demonstrate i) HIV-1 Tat enhances the SHM process in B cells in vitro when introduced exogenously; ii) the enhancing effect of HIV-1 Tat on SHM can be combined with other cellular SHM promoting conditions; iii) Tat family proteins from other members in the retrovirus family can also promote SHM; iv) the enhancing effect of Tat on SHM relies on its eukaryotic transcription machinery interacting domain; and v) sequence variants of Tat and other similar proteins that retain their interaction capacity with the transcriptional complex can exert a similar effect on SHM.

The example uses one of the SHM proficient human B cell lines known as Ramos cell line and its derivatives including: i) a subclone bearing an early stop codon in the immunoglobulin coding V region; ii) a reporter cell line in which a reporter cassette in the endogenous immunoglobulin V region and wherein the SHM process is controlled by 4-hydroxytamoxifen-induced nuclear localization of AID-ER fusion protein [also see Ref 1].

Figures 2A, 2B:
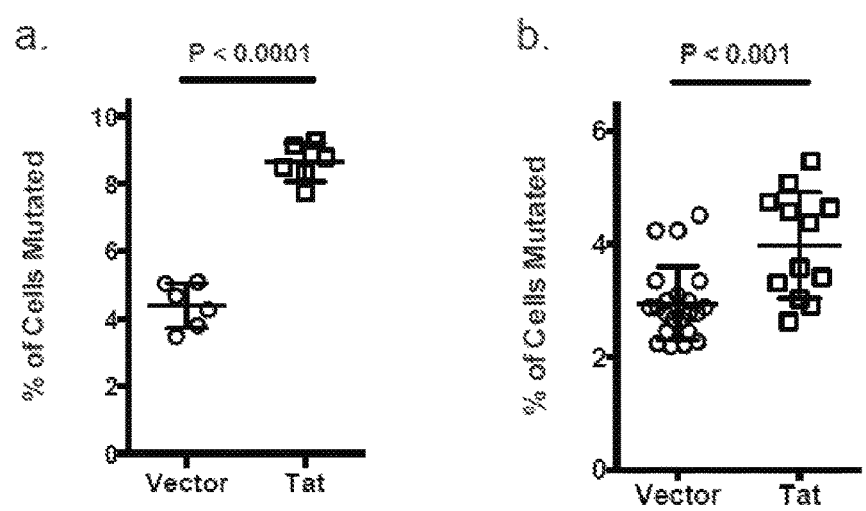
FIG. 2A-2B: Exogenous expression of HIV-tat increases B cell SHM: a) Ramos reporter cells were transduced by lentiviral particle carrying either a control vector or tat expressing vectors. Successfully transduced cells were induced and the rate of SHM was assessed 7 days later. Data represents a compiled analysis of 3 independent transductions with total of 6 independent induction experiments. b) Ramos reporter cells were transfected with eukaryotic expression vectors of tat or an empty vector control. 6 independent tat expressing clones and 9 control clones carrying the empty vector were induced for SHM to assess SHM rate. Data represents the compiled analysis of two independent induction experiments.

In most experiment, exogenous genes or shRNAs were delivered into Ramos B cells by lentiviral mediated transduction, except for the experiment described in FIG. 2b where electroporation was used. In the case of exogenous gene expression, a pCDH vector (System Biosciences, CA) was used and genes were cloned into the construct by inserting the PCR product into multiple cloning sites in the vector. shRNA constructs against human Spt5 were as published in [Ref 1].

In the case of exogenous expression of Tat family members and their variants, gene fragments encoding the corresponding protein were introduced into Ramos reporter cell line using lentiviral particles prepared through common practice. The eGFP cassette in the pCDH vector was used as an indication of successful delivery of the exogenous genes of interest. Ramos cells that successfully received the vector were sorted based on eGFP using flow cytometry.

The SHM process in the AID-ER fusion protein bearing Ramos cells is tunable through the control of subcellular localization of AID-ER molecules. In the absence of 4-hydroxytamoxifen, the AID-ER fusion protein remains in the cytosol and is not able to mediate SHM. In the presence of 4-hydroxytamoxifen, the AID-ER fusion protein is transported into nuclear to mediate SHM.

In an example, the HIV protein Tat in a human germinal center like B cell line (Ramos) significantly increased the SHM mutation rate at the IgH-V region (FIG. 2a). Although the initial observation was based on lentiviral delivery of Tat into Ramos cells, other vectors can be used. A pCDNA-tat eukaryotic expression vector had a very similar effect, indicating that the Tat protein itself, independent of other retroviral genomic components, is sufficient to promote SHM (FIG. 2b).

Figure 3:
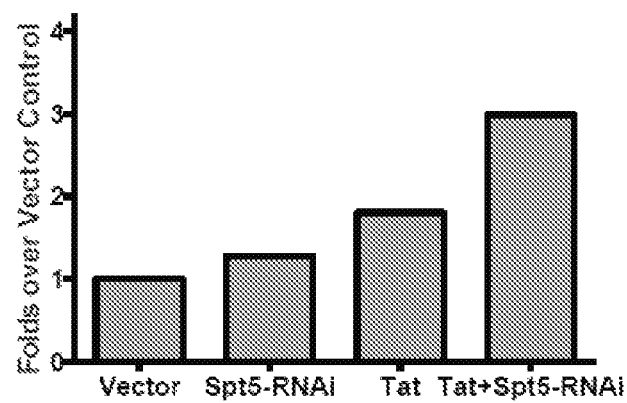
FIG. 3: Synergistic effect of Tat with other factors to promote high-level SHM. Ramos cells were transduced with vector controls, shRNA against Spt5, exogenous expression of Tat, and both. The rates of SHM were then assessed after 7 days of induction through Tamoxifen mediated nuclear localization of AID-ER fusion protein.

In the other example, the question of whether the enhancing effect of Tat on SHM at Ig loci can be combined with other method of enhancing SHM through the manipulation of endogenous cellular factors was investigated. A recent publication from this laboratory showed that the reduction of cellular Spt5 level could increase SHM efficiency at Igh loci [1]. When the expression Tat was combined with shRNA-mediated knockdown of Spt5, a synergistic 3-fold increase of SHM was observed (FIG. 3).

Figure 4:
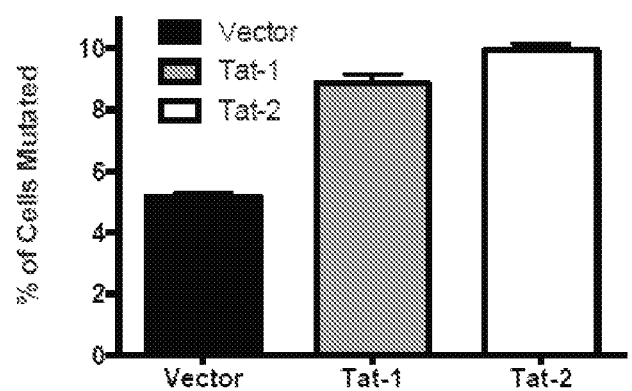
FIG. 4: Tat 1 and Tat-2 expression vectors were transduced into Ramos reporter cells and those cells that were transduced successfully were then induced and the rate of SHM was assessed 7 days later.

In another example, Tat-2 protein from HIV-2 virus that shares less than 30% sequence identity but shares the capacity of binding eukaryotic transcriptional machinery was introduced into Ramos reporter cell line and was able to enhance SHM to a level that was equal to HIV-1 Tat mediated effect (FIG. 4).

In another example, HIV-1 tat protein, its various truncated forms and the corresponding C22G mutation form were introduced into the Ramos reporter cells. The 48aa form of Tat-1 is the smallest unit that retains the capacity to bind eukaryotic transcription machinery. The C22G single amino acid mutation is known to abolish the interaction between Tat-1 protein and the eukaryotic transcription machinery. While all truncated forms enhance SHM, the C22G mutant form does not (FIG. 5).

Figure 5:
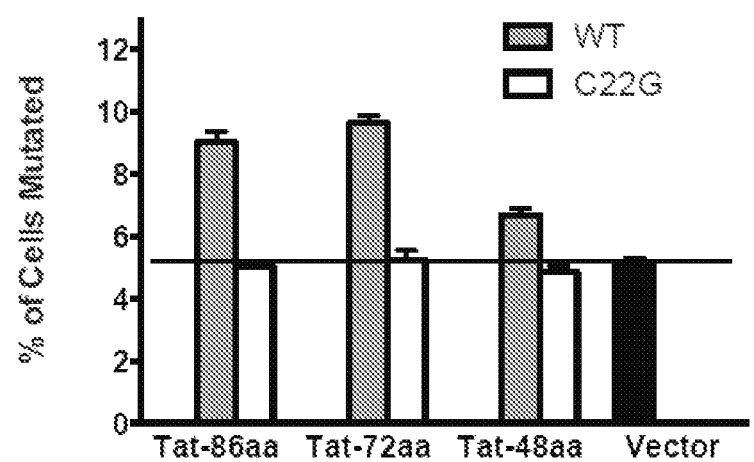
FIG. 5: The sub-domain of Tat that interacts with eukaryotic transcription factors is essential for the enhancing effect of Tat on SHM: empty vector, different truncated versions of Tat and Tat with a single amino acid mutation (C22G) form that eliminates the interaction between Tat and transcriptional machinery were introduced into the Ramos reporter cell line. Successfully transduced cells were induced and the rate of SHM was assessed 7 days later. Data is a representative example of 4 independent experiments.

Based on the observation in FIGS. 4 and 5, sequence variants of Tat and other similar proteins that retain their interaction capacity to transcriptional complex could possess similar enhancing effect on SHM like Tat-1 protein from HIV-1 virus.

Since the SHM reporter Ramos cell line is based on the exogenously induced expression of AID-ER fusion protein, it has a ~4 fold higher of SHM rate than the spontaneous SHM rate in parental Ramos cells (FIG. 1). In combination with the over expression of Tat and the knockdown of Spt5, at least an ~12 fold increase of the SHM has been achieved in these modified Ramos cells over the original parental cell line that were used to generate antibody against model streptavidin antigen as demonstrated previously [2].

This provides a new venue to enhance the SHM of the immunoglobulin gene, which will improve the efficiency of developing antigen-specific antibodies of preferred affinities. Such a platform is superior to current in vitro antibody development platforms on the market in view of its high efficiency and its capacity to obtain post-translational modifications of an antibody that occurs in human B cells.

REFERENCES

1. A source of the single-stranded DNA substrate for activation-induced deaminase during somatic hypermutation. Wang X, Fan M, Kalis S, Wei L, Scharff M D. *Nat Commun.* 2014 Jun. 13; 5:4137.
2. Generation and iterative affinity maturation of antibodies in vitro using hypermutating B-cell lines. Cumbers S J, Williams G T, Davies S L, Grenfell R L, Takeda S, Batista F D, Sale J E, Neuberger M S. *Nat Biotechnol.* 2002 November; 20(11):1129-34

What is claimed is:

1. A method of increasing somatic hypermutation of an immunoglobulin loci comprising effecting expression of a Tat protein in (i) an isolated mammalian immunoglobulin-producing cell, or (ii) an isolated immunoglobulin-producing cell of a cell line derived from a mammal, in an amount effective to increase somatic hypermutation of an immunoglobulin loci.

2. The method of claim 1, wherein expression is effected in an isolated mammalian immunoglobulin-producing B cell.

3. The method of claim 1, wherein expression is effected in the isolated immunoglobulin-producing cell of a cell line derived from a mammal.

4. The method of claim 3, wherein the isolated immunoglobulin-producing cell of a cell line derived from a mammal is a cell that does not constitutively express immunoglobulins, but which has been genetically engineered to express immunoglobulins.

5. The method of claim 3, wherein the isolated immunoglobulin-producing cell of a cell line derived from a mammal is a Ramos cell line.

6. The method of claim 1, wherein the isolated immunoglobulin-producing cell of a cell line derived from a mammal is a hybridoma.

7. The method of claim 1, wherein the cell secretes immunoglobulins.

8. The method of claim 1, wherein the cell expresses immunoglobulins on a cell surface thereof.

9. The method of claim 1, wherein the expression of the isolated exogenous protein is of a retroviral protein in the cell is effected by contacting the cell with a vector encoding the isolated retroviral protein.

10. The method of claim 1, wherein the isolated retroviral protein is an HIV-2 Tat protein.

11. The method of claim 9, wherein the vector is a lentiviral vector.

12. The method of claim 9, wherein the vector is an adenoviral vector.

13. The method of claim 1, wherein the expression of the HIV Tat protein in the cell is effected by contacting the cell with a pCDNA-tat eukaryotic expression vector encoding the exogenous HIV Tat protein.

14. The method of claim 1, further comprising recovering one or more immunoglobulins produced by the cell of (i) or (ii) subsequent to effecting expression of the isolated exogenous protein therein.

15. The method of claim 14, further comprising screening the one or more immunoglobulins for activity against a predetermined antigen.

16. The method of claim 1, further comprising reducing expression of Spt5 in the cell of (i) by contacting the cell with a RNAi nucleic acid directed to Spt5.

17. The method of claim 16, wherein the RNAi nucleic acid directed to Spt5 is a siRNA or an shRNA.

18. The method of claim 17, wherein the RNAi nucleic acid is an shRNA delivered by a vector.

* * * * *